United States Patent [19]

Seliskar et al.

[11] Patent Number: 4,794,230
[45] Date of Patent: Dec. 27, 1988

[54] LOW-PRESSURE WATER-COOLED INDUCTIVELY COUPLED PLASMA TORCH

[75] Inventors: Carl J. Seliskar, Cincinnati; David K. Warner, Centerville, both of Ohio

[73] Assignee: The United States of America as represented by the United States Department of Energy, Washington, D.C.

[21] Appl. No.: 580,983

[22] Filed: Feb. 16, 1984

[51] Int. Cl.[4] .............................................. B23K 9/00
[52] U.S. Cl. ........................ 219/121.52; 219/121.51; 219/121.49; 219/121.5; 315/111.51
[58] Field of Search ...... 219/121 P, 121 PQ, 121 PN, 219/121 PM, 121 PP, 76.16, 10.55 R; 315/111.21, 111.51

[56] References Cited

U.S. PATENT DOCUMENTS

| | | | |
|---|---|---|---|
| 3,296,410 | 1/1967 | Hedger | 219/121 PR |
| 3,467,471 | 9/1969 | Greenfield et al. | 219/121 PR |
| 3,514,604 | 5/1970 | Grojean | 219/10.55 R |
| 3,635,561 | 1/1972 | Bordonati et al. | 356/85 |
| 3,694,618 | 9/1972 | Poole et al. | 219/121 PR |
| 3,731,047 | 5/1973 | Mullen et al. | 219/121 PR |
| 3,958,883 | 5/1976 | Turner | 219/121 P |
| 4,225,235 | 9/1980 | Anderson et al. | 356/316 |
| 4,266,113 | 5/1981 | Denton et al. | 219/121 PQ |
| 4,293,220 | 10/1981 | Denton et al. | 356/316 |

Primary Examiner—M. H. Paschall
Attorney, Agent, or Firm—George H. Libman; James H. Chafin; Judson R. Hightower

[57] ABSTRACT

An inductively coupled plasma torch is provided which comprises an inner tube, including a sample injection port to which the sample to be tested is supplied and comprising an enlarged central portion in which the plasma flame is confined; an outer tube surrounding the inner tube and containing water therein for cooling the inner tube, the outer tube including a water inlet port to which water is supplied and a water outlet port spaced from the water inlet port and from which water is removed after flowing through the outer tube; and an r.f. induction coil for inducing the plasma in the gas passing into the tube through the sample injection port. The sample injection port comprises a capillary tube including a reduced diameter orifice, projecting into the lower end of the inner tube. The water inlet is located at the lower end of the outer tube and the r.f. heating coil is disposed around the outer tube above and adjacent to the water inlet.

6 Claims, 1 Drawing Sheet

U.S. Patent  Dec. 27, 1988  4,794,230
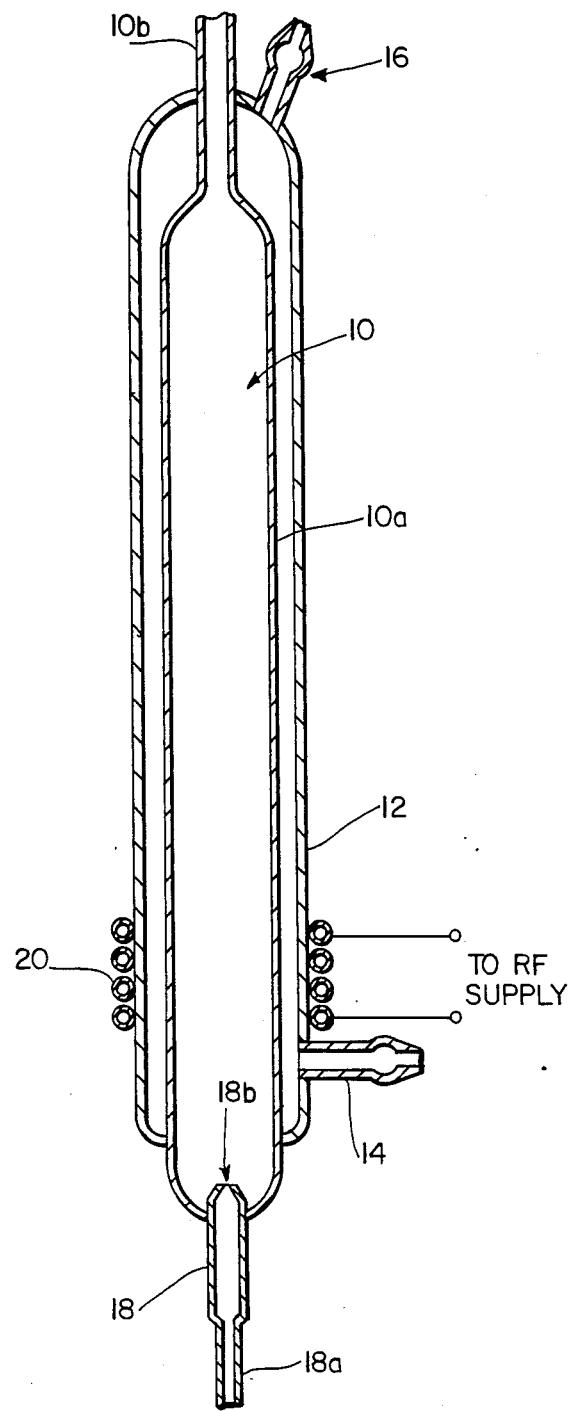

LOW-PRESSURE WATER-COOLED INDUCTIVELY COUPLED PLASMA TORCH

FIELD OF INVENTION

The present invention relates to an improved inductively coupled plasma (ICP) torch which is particularly adapted for used in the analysis of the concentration of many stable isotopes. The United States Government has rights in this invention pursuant to Contract No. De-AC04-76DP00053 between the Department of Energy and Monsanto Research Corporation.

BACKGROUND OF THE INVENTION

Currently there is no easy-to-use, inexpensive method for measuring the concentrations of many stable isotopes. As enriched stable isotopes become more available for many important agricultural, medical and physical studies, the lack of such a method will prevent the more general usage of these valuable chemical tracers.

Inductively coupled plasma (ICP) emission spectroscopy is an established ultrasensitive analytical method which has been used to measure trace metals at the sub-parts-per-billion level. A typical commercially available ICP emission spectrometer consists of three major components, viz., a microcomputer and sample introduction system, the plasma source system, and the emission spectrometer and detection system. Trace metal analysis is achieved by quantitatively measuring atomic optical emission from the plasma.

Examples of prior art ICP devices include those disclosed in U.S. Pat. Nos. 3,467,471 (Greenfield et al); 4,293,220 (Denton et al); 4,266,113 (Denton et al); and 3,958,883 (Turner). Examples of plasma torches which are driven by microwave radiation include those disclosed in U.S. Pat. Nos. 4,225,235 (Anderson et al) and 3,843,257 (Wooten). Other patents of possible interest include 3,514,604 (Trojean) and 3,635,561 (Bordonali et al). Briefly considering some of these patents, the Greenfield et al patent discloses an inductively coupled plasma torch which is used as a spectroscopic source and which employs an "insulating fluid" that surrounds the plasma. The "insulating fluid" is apparently a coolant gas, although, as discussed below, mention is also made of the use of water for this purpose. Reference is made elsewhere in the patent to water cooling of the induction coil. The requirements of this torch include high gas flow and high power. The Denton et al patents disclose ICP torches similar to that of the Greenfield et al patent and which likewise are characterized by high r.f. power demands, high gas flow rate and a water cooled r.f. induction coil. The torch is designed to minimize molecular band emission. The torch of the Turner patent is also similar, the torch operating at high pressure and being designed to maximize atomic emission and minimize molecular emission. As noted above, the Anderson et al and Wooten patents concern torches which are driven by microwave radiation and both are concerned with a design and operation of the torch which minimizes molecular emission. The significance of the teachings of the prior art and the differences between the prior art and the present invention will be discussed below.

SUMMARY OF THE INVENTION

In accordance with the invention, an improved ICP torch is provided which possesses a number of advantages over prior art torches of the same basic type. The improved ICP torch of the invention provides a number of key features. First, the torch is water cooled and the cooling provided by water is greatly enhanced as compared with argon or air. (As noted above, the Greenfield et al patent mentions, in one instance, the use of water as the "insulating fluid" employed therein. However, the torch actually disclosed therein is not capable of employing water as a coolant and the entire thrust of the patent involves the use of an insulating gas.) Second, the sample injection port is constructed so as to minimize the plasma extension into the back-flow region of the torch. Third, the ICP torch of the invention is capable of operation over a wide range of (reduced) pressures with a variety of carrier gases, e.g., argon, helium, neon and krypton. Prior art ICP torches are either unable to operate with helium or are only able to do so under very specialized conditions. The low-pressure carrier gas flow provided serves to minimize the optical congestion caused by atomic/molecular collision emissions and permits detection of the emission lines produced by the isotopes in the atomized samples injected into the plasma.

The torch of the invention is constructed to fit commercially available ICP radio-frequency (r.f.) generators and commercially available ICP spectrometers. Further, the torch is usable with only a simple laboratory vacuum pump. In this regard, it is noted that the simplicity of the torch of the invention enables the use thereof as a new detector unit for gas chromatographs. For example, the torch of the invention does not require the large volume of make-up gas (usually argon or helium) needed to operate conventional ICP torches.

Although not limited to such a use, the plasma torch of the invention is, as discussed below, specifically constructed to adapt commercial ICP instruments to permit the use thereof in stable isotope analyses. The usage, which is afforded by the characteristics of the torch of the invention, has significant commercial value, particularly in medical areas.

According to a preferred embodiment of the invention, an inductively coupled plasma torch is provided which comprises an inner tube, including a sample injection port to which the sample to be tested is supplied, comprising an enlarged central portion in which the plasma flame is confined; an outer tube surrounding the inner tube and containing water therein for cooling the inner tube, the outer tube including a water inlet port to which water is supplied and a water outlet port spaced from the water inlet port and from which water is removed after flowing through the outer tube; and an r.f. heating coil for exciting a plasma in the gas passing into the tube through the sample injection port. Preferably, the sample injection port comprises a capillary tube, including a reduced diameter orifice, projecting into the lower end of the inner tube. Advantageously, the inner tube includes at the upper end thereof an open ended portion of reduced diameter as compared with the central portion. Preferably, the water inlet is located at the lower end of the outer tube, and the r.f. induction coil is disposed around the outer tube above and adjacent to the water inlet, with the water outlet being located at the top of the outer tube.

Other features and advantages of the invention will be set forth in, or apparent from, the detailed description of a preferred embodiment which follows.

BRIEF DESCRIPTION OF THE DRAWINGS

The single FIGURE in the drawings is a cross-sectional view of an ICP torch constructed in accordance with a preferred embodiment of the invention.

DESCRIPTION OF THE PREFERRED EMBODIMENT

Referring to the single FIGURE in the drawings, the inductively coupled plasma torch of the invention basically comprises an inner plasma containing tube 10 and an outer closed water containing tube 12. The outer tube 12 includes a water inlet 14 at the lower end thereof and water outlet 16 at the upper end thereof and thus the water coolant flows along the length of inner tube 10.

The inner tube 10 is disposed centrally of outer tube 12 and comprises an elongate main portion 10a which necks down at the upper end to a upper portion 10b of substantially more narrow diameter. A short capillary tube 18, which forms a sample injection port, penetrates the lower, generally hemispherical end of inner tube 10. The capillary tube 18 includes lower inlet portion 18a of reduced diameter and the upper end of tube 18 is necked down to approximately one-half of the diameter to form an inlet orifice 18b.

In an exemplary embodiment, tube body 10a has a nominal diameter of ¾ inch while outer tube 12 has a maximum diameter of 15/16 inch. Upper tube portion 10b has an outside diameter of ⅜ inch. The capillary tube 18 is a ⅜-inch tube and thus the diameter of the orifice 18b is about 3/16 inch. The inlet portion 18a of capillary tube has an outside diameter of ¼ inch. The overall length of the inner tube 10 is about 12 inches while the length of the capillary tube is about 1 inch. All components are preferably made of transparent quartz.

An r.f. coil 20 is wrapped around the outer tube 12 just above water inlet 14 and serves to induce the plasma in the gas passing into the tube 10 through orifice 18b. The capillary tube 18 is connected to the plasma gas and sample source (not shown).

As set forth above, an important feature of the invention is the low pressure operation provided. A mean plasma gas pressure of 0.5 to 15 torr for the region tested has been used which covers the isotope analysis plus GC region. The gas flow rate is 17–20 standard cm$^3$/min at 15 torr mean pressure. The typical coolant (water) flow rate is 0.5 gal/min.

The input power coupled to the r.f. coil 20 is low as compared with prior art devices and the power level at which the torch is operated is such as to preclude boiling the water coolant. A typical power coupling level is 150 W at a frequency of 27.12 MHz, with the test range being 50–250 W at that frequency.

It is noted that the torch system of the invention is capable of measuring hydrogen and deuterium isotopes at least two orders of magnitude better than conventional mass spectrometry. It is also noted that the system is capable of providing measurements of contaminants in gas mixtures. For example, the presence of nitrogen from air contamination of argon can be detected by measuring nitrogen (molecular) emission.

As stated above, the plasma torch of the invention is constructed to fit the commercially available ICP radiofrequency generators. The torch is usable with only a simple laboratory vacuum pump. Indeed, the simplicity thereof makes the torch usable as a new detector unit for gas chromatographs. As explained, the plasma torch is designed to adapt to commercial ICP instruments to allow them to be used for stable isotope analyses, and this intended usage, which depends on the operating and construction characteristics of the torch of the invention, has significant commercial value, especially in the medical area. As set forth hereinabove, yet another potential commercial use of the new torch appears to be as the main component of a detector unit for gas chromatographs.

Although the invention has been described relative to an exemplary embodiment thereof, it will be understood by those skilled in the art that variations and modifications can be effected in this exemplary embodiment without departing from the scope and spirit of the invention.

We claim:

1. An inductively coupled low-pressure plasma torch consisting of:
    - an transparent inner tube comprising an elongate main portion in which the plasma flame is confined extending from an input end to an output end, the output end including a portion having a neck of narrower diameter than the diameter of said main portion;
    - short capillary tube means penetrating the input end of said inner tube for injecting plasma gas and samples into said inner tube through an inlet orifice, said inlet orifice being adjacent the input end of said inner tube;
    - an transparent outer tube surrounding said inner tube and containing water therein for cooling the inner tube, said outer tube including a water inlet port to which water is supplied and a water outlet port spaced from said water inlet port from which water is removed after flowing through said outer tube; and
    - r.f. induction coil means surrounding said outer tube for exciting a plasma in the gas passing into said inner tube.

2. An inductively coupled plasma torch as claimed in claim 1 wherein said outer tube extends from a lower end near the input end to an upper end at said neck portion of said inner tube.

3. An inductively coupled plasma torch as claimed in claim 2 wherein said water inlet is located adjacent the lower end of said outer tube and said r.f. induction coil is relatively short as compared to the length of said inner tube and is disposed around said outer tube adjacent to said water inlet.

4. An inductively coupled plasma torch as claimed in claim 3, wherein said water outlet is located at the upper end of the outer tube.

5. An inductively coupled plasma torch as claimed in claim 4, wherein said main portion of said inner tube is generally hemispherical at the input end thereof and said sample injection port comprises a capillary tube and terminates in an orifice of reduced diameter as compared to the main body of said capillary tube.

6. An inductively coupled plasma torch as claimed in claim 5 wherein the diameter of said orifice is approximately one-half of the diameter of said main body.

* * * * *